(12) United States Patent
Lichtscheidl et al.

(10) Patent No.: US 7,413,547 B1
(45) Date of Patent: Aug. 19, 2008

(54) REFERENCE SENSOR CORRECTION FOR IMPLANTABLE SENSORS

(75) Inventors: Gregg R. Lichtscheidl, Roseville, MN (US); Perry A. Mills, Arden Hills, MN (US)

(73) Assignee: Transoma Medical, Inc., Arden Hills, MN (US)

( * ) Notice: Subject to any disclaimer, the term of this patent is extended or adjusted under 35 U.S.C. 154(b) by 196 days.

(21) Appl. No.: 10/984,111

(22) Filed: Nov. 8, 2004

(51) Int. Cl.
*A61B 5/00* (2006.01)
(52) U.S. Cl. ........................................ 600/486; 600/485
(58) Field of Classification Search ........................ None
See application file for complete search history.

(56) References Cited

U.S. PATENT DOCUMENTS

| | | | |
|---|---|---|---|
| 4,846,191 A | 7/1989 | Brockway et al. | |
| 6,890,303 B2 * | 5/2005 | Fitz | 600/486 |
| 7,112,170 B2 * | 9/2006 | Schock et al. | 600/18 |
| 2005/0182330 A1 * | 8/2005 | Brockway et al. | 600/486 |

OTHER PUBLICATIONS

U.S. Appl. No. 10/717,179, filed Nov. 17, 2003, Zwiers et al.

* cited by examiner

*Primary Examiner*—Robert L Nasser
(74) *Attorney, Agent, or Firm*—Fish & Richardson P.C.

(57) ABSTRACT

Implantable medical device systems and methods for measuring a body parameter utilizing an implantable functional pressure sensor and a fixed reference sensor, wherein the reference sensor compensates for drift of all other components in the measurement system other than the functional sensor. The reference sensor provides a basis for comparison to determine if and to what extent the electronic components, for example, have drifted over time, and thus provides a basis for correcting functional measurements and improving long term measurement accuracy.

32 Claims, 6 Drawing Sheets

REFERENCE SENSOR CORRECTION FOR IMPLANTABLE SENSORS

GOVERNMENT LICENSE RIGHTS

Portions of the subject matter disclosed herein were developed under Grant No. 8R44EB00354 awarded by the U.S. Department of Health and Human Services, National Institutes of Health, and therefore, the U.S. Government may have rights to certain claimed inventions.

CROSS-REFERENCE TO RELATED APPLICATIONS

The present application is related to U.S. patent application Ser. No. 10/717,179, filed Nov. 17, 2003, entitled Implantable Pressure Sensors, the entire disclosure of which is incorporated herein by reference.

FIELD OF THE INVENTION

The present invention relates to drift correction of implantable sensing devices, such as implantable pressure sensors.

BACKGROUND OF THE INVENTION

An example of an implantable pressure sensing device is disclosed in U.S. Pat. No. 4,846,191 to Brockway et al. Such an implantable pressure sensing device utilizes a sensor assembly including a pressure sensor and a fluid-filled catheter. The fluid-filled catheter refers pressure from a measurement site to the pressure sensor which converts the pressure signal into an electrical signal.

With a chronically implantable pressure sensing device such as that described in Brockway et al. '191, the stability of the device is preferably high, thus reducing the adverse effects of drift that lead to measurement inaccuracies over time. For example, the pressure sensor in a commercially available pressure measurement device designed to be implanted in mice (Data Sciences International Model No. PAC-20) has a specified maximum drift rate of 2.0 mmHg per month, and has been observed to have an average drift rate of 0.75 mmHg per month, with a best known drift rate of 0.25 mmHg per month. For some applications, such as chronically implanted human devices, it is desirable to have even lower drift rates.

SUMMARY OF THE INVENTION

In a pressure sensing device or system, a number of components contribute to drift. For example, in such a system, both the pressure sensor and the associated electronics may contribute significantly to drift. U.S. patent application Ser. No. 10/717,179, filed Nov. 17, 2003, entitled Implantable Pressure Sensors, addresses drift associated with the pressure sensor. However, there is an ongoing need to address drift associated with the other components of the system such as electronic components.

To address this need, the present invention provides a variety of improvements to the design of chronically implantable pressure sensors. In exemplary embodiments, an implantable medical device (IMD) system and method is described for measuring a body parameter utilizing an implantable functional sensor and a fixed reference (or "dummy") sensor, wherein the reference sensor compensates for drift of all components in the measurement system other than the functional sensor and the reference sensor. The reference sensor provides a basis for comparison to determine if and to what extent the electronic components, for example, have drifted over time, and thus provides a basis for correcting functional measurements and improving long term measurement accuracy. Illustrative embodiments of IMD systems and methods utilizing a reference sensor are described in more detail hereinafter.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
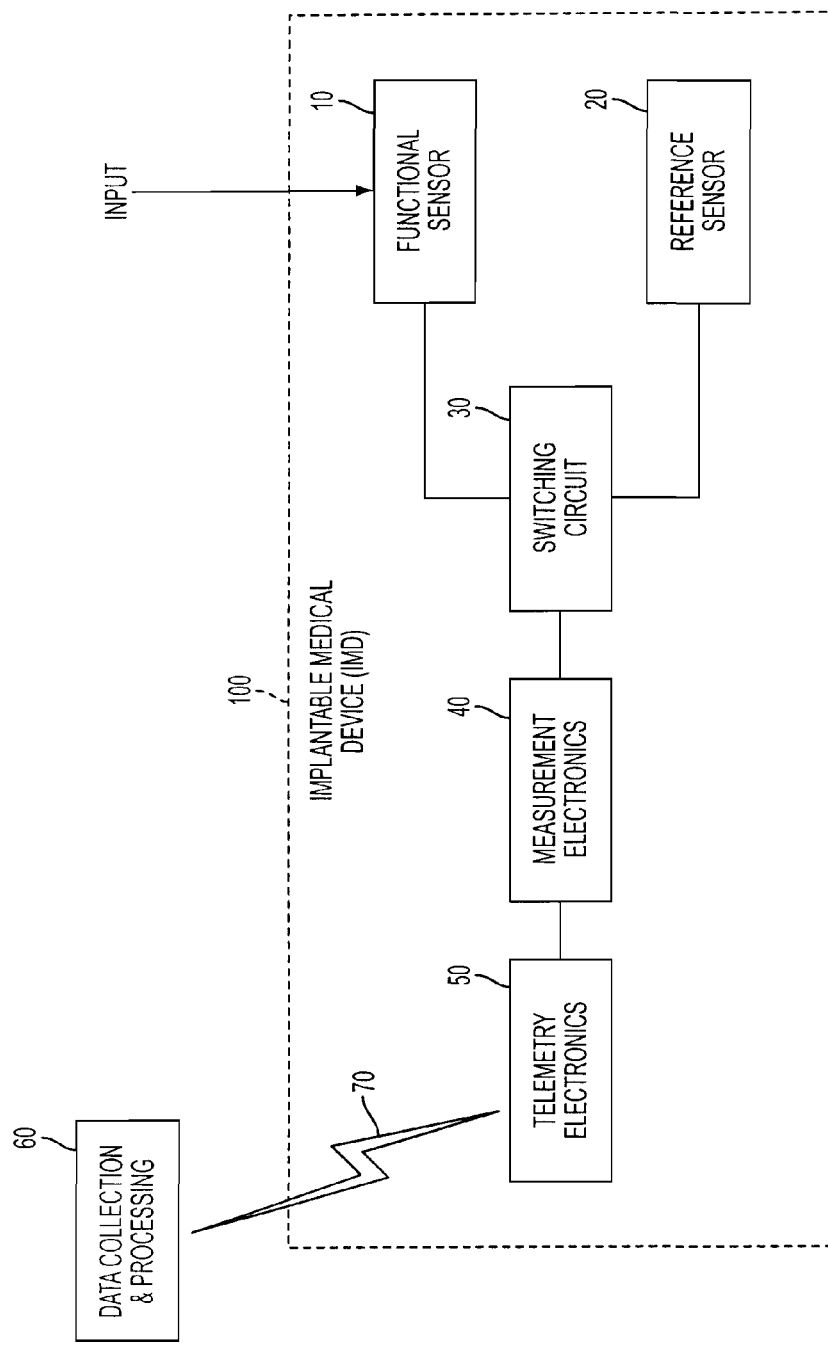
FIG. 1 is a schematic block diagram of an implantable medical device (IMD) incorporating a functional sensor and a reference sensor.

With reference to FIG. 1, an exemplary embodiment of an implantable medical device 100 is shown schematically. The IMD includes a functional sensor 10 which may comprise a pressure sensor for measuring a variable body parameter such as blood pressure, intracranial pressure, etc. The functional sensor 10 may be connected to a measurement electronics module 40 via switching circuit 30. The measurement electronics module 40 may comprise, for example, a signal processing circuit. The measurement electronics module 40, in addition to other electronic components other than the functional sensor 10, may be susceptible to drift over time, and therefore a reference sensor 20 may be used to detect and/or compensate for such drift. The reference sensor 20 may be fixed and stable, or otherwise subject to less drift over time than the measurement electronics 40, to enable drift in the measurement electronics 40 (or other electronic components subject to drift) to be readily detected. In this context, the reference sensor 20 may be fixed such that it has a relatively constant value and does not significantly vary with changes to it's environment (e.g., constant value with changes in pressure, temperature, etc.). In this context, fixed does not mean that the value of the reference sensor cannot be changed by trimming or programming, for example.

The reference sensor 20 and the switching circuit 30 are shown as discrete components, but may be combined or partitioned with respect to the functional sensor 10 and the measurement electronics module 40 in any suitable manner. Optionally, the measurement electronics module 40 may be connected to a telemetry electronics unit 50 which transmits sensor data to a data collection and processing unit 60 via wireless link 70. The measurement electronics module 40 and/or the data collection and processing unit 60 may incorporate memory and a processor for storing and executing data processing programs/algorithms such as the correction function, the transfer function and/or other functions described hereinafter, or the same may be incorporated into the hardware of the electronics module 40 and/or the data collection and processing unit 60.

FIG. 1 generally illustrates an example of a system including an implantable medical device 100 and associated method to reduce measurement drift by using a low-drift reference or "dummy" sensor 20. The reference sensor 20 is connected to the measurement circuitry 40 to create a reference value to be compared with the measurement using the functional sensor 10. In other words, the reference sensor 20 provides a basis for comparison to determine if and to what extent the measurement electronics 40, for example, have drifted over time, and thus provides a basis for correcting functional measurements taken by functional sensor 10 to improve long term measurement accuracy.

This approach effectively reduces drift contributed by all components in the system including the implantable device 100 (other than the functional sensor 10 and reference sensor 20) and any component that precedes the correction function. Components that may contribute to drift include measurement electronics 40, transmitter electronics 50, external time-to-digital conversion circuitry as well as other sources. This approach has substantial benefit in systems where the components of the implantable device 100 other than the functional sensor 10 cause a significant percentage of long-term drift, particularly where the functional sensor 10 drift has been reduced such that the drift of the rest of the system becomes a significant percentage of overall drift.

Generally speaking, the functional sensor 10 measures an electrical parameter that may be correlated to or is otherwise indicative of a body parameter. For example, the functional sensor may change an electronically measurable parameter such as resistance, electrical output (voltage and/or current), etc. in response to changes in the body parameter. The correlation of the electrical parameter to the body parameter may be defined as a transfer function or calibration function which equates the value of the electrical parameter (or measurement signal) to a value of the body parameter. The transfer function may be predefined and programmed into the measurement electronics module 40. At some time prior to use for measuring the body parameter, such as prior to implantation or during manufacture, the transfer function may be defined. To obtain a value of the body parameter, the transfer function may be applied to the value of the electrical parameter as measured by the functional sensor 10.

In the context of a linear transfer function such as $y=ax+b$, where "y" is the body parameter (e.g., pressure) and "x" is the measured parameter (e.g., voltage) the scale factor corresponds to the slope ("a") and the offset value corresponds to the y-axis intersection ("b"). To correct for drift of the measurement electronics 40 or other source of drift, the measurement electronics 40 (and/or the data collection and processing electronics 50) may apply a correction to the offset value and/or scale factor of the transfer function relating the measured value of the functional sensor 10 to the body parameter. Thus, for example, the offset value may be corrected by a difference (if any) between a prior value of the reference sensor 20 to a current value of the reference sensor 20. If there is a difference in the value of the reference sensor 20, the difference is representative of offset drift of the measurement electronics 40, and the difference may be generically referred to a drift value or a value indicative of drift. The difference may be subtracted from the measurement value of the functional sensor 10 to obtain a corrected measurement value that is compensated for drift of the electronics.

With the offset value and scale factor approaches, the measurement electronics 40 or data collection and processing unit 60 may include a corrector (e.g. correction circuit or correction function) which compares (e.g., subtracts) the prior value(s) of the reference sensor 20 to the current value(s) of the reference sensor 20 to obtain the offset value or scale factor (scale factor correction requires comparison of values at different sensor output levels). The corrector may comprise hardware (e.g., circuit) or software (e.g., executable program/algorithm) contained in the electronics module 40 and/or the data collection and processing unit 60.

The prior value(s) of the reference sensor 20 may be obtained at some time prior to taking a measurement using the functional sensor 10, such as prior to implantation or during manufacture when the transfer function is defined. The current value of the reference sensor 20 refers to the value of the reference sensor 20 taken at or about the same time as a measurement is taken with the functional sensor. A switching circuit 30 may be used to obtain both the measurement from the functional sensor 10 and the current measurement from the reference sensor 20.

As an alternative, the transfer function may be defined as a function of the value of the reference sensor 20. With this approach, an initial value of the reference sensor 20 may be obtained at or about the time the transfer function is defined, such as prior to implantation or during manufacture, or reference measurements may be taken over a range of time. At or about the same time as a measurement is to be taken using the functional sensor 10, a measurement may be taken using the reference sensor 20 and applied to the transfer function. For example, immediately before or after a measurement is to be taken using the functional sensor 10, and prior to application of the transfer function, a measurement may be taken using the reference sensor 20 and applied to the transfer function. In other words, the transfer function may include a variable comprising a current reference sensor measurement, such that when the transfer function is applied to the measurement of the functional sensor 10, the result is automatically corrected for drift of the electronics.

Those skilled in the art will appreciate that the preceding correction schemes are illustrative and other mathematical approaches may be utilized.

The method of reducing measurement drift by using a low-drift reference or "dummy" sensor 20 may be applied to a variety of functional sensor types including pressure sensors, temperature sensors, flow sensors, or any other sensor for measuring a body parameter, but is described herein in terms of a pressure sensor for purposes of illustration, not necessarily limitation. In terms of pressure sensors, this approach may be used with various types including piezoresistive, strain gauge, piezoelectric, etc., but is described herein with reference to FIGS. 2A-2C in the context of a silicon piezoresistive wheatstone bridge type pressure sensor for sake of illustration.

Figure 2A:
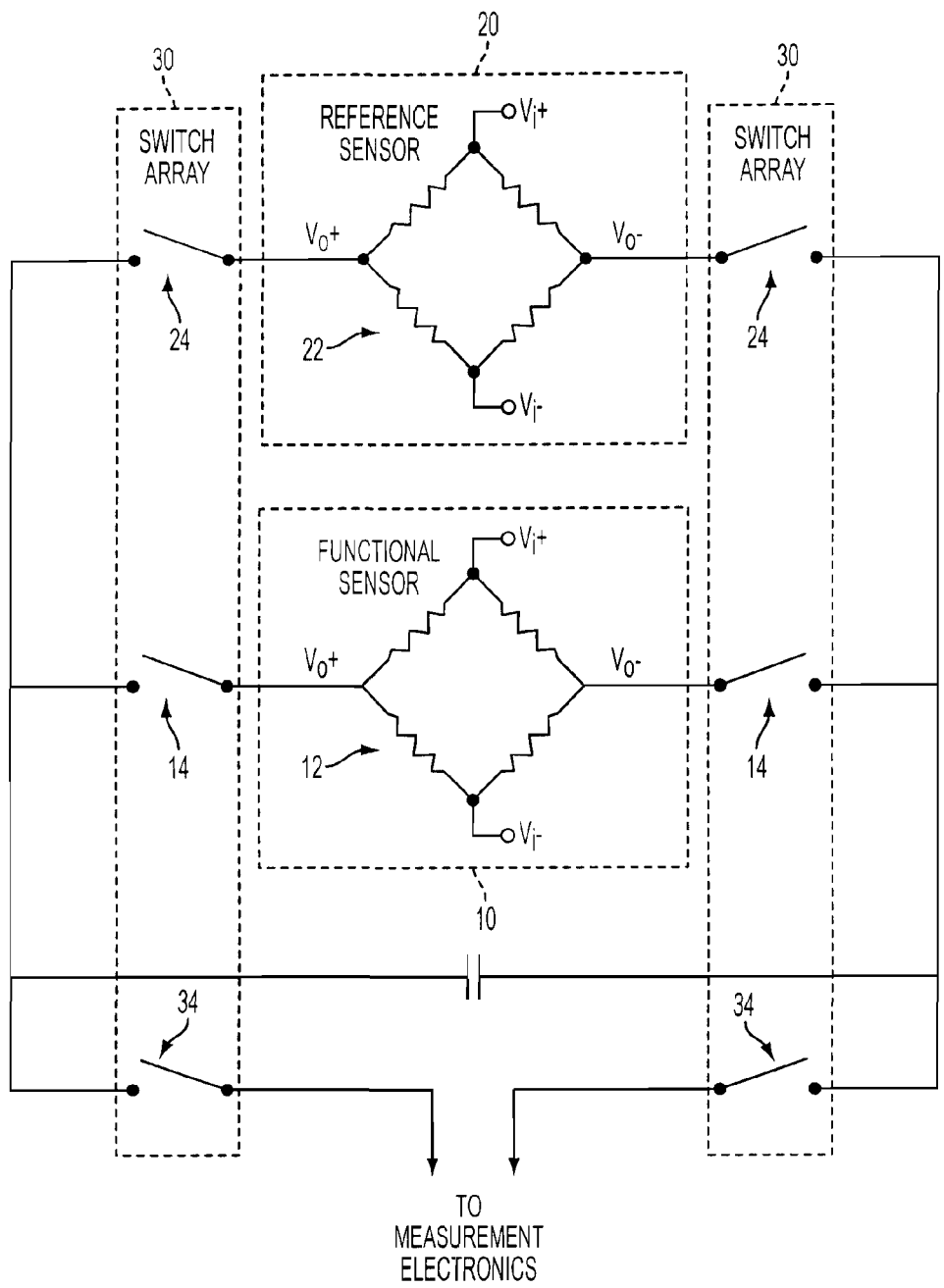
FIGS. 2A-2C illustrate examples of various functional and reference sensor arrangements.

With reference to FIG. 2A, the functional sensor 10 is shown to be a silicon piezoresistive wheatstone bridge 12 for measuring pressure. To measure pressure, an excitation signal may be initially applied (continuously or strobed for power conservation) by the measurement electronics 40 to the wheatstone bridge 12 across $V_i+$ and $V_i-$. The output of the wheatstone bridge 12 across $V_o+$ and $V_o-$ is proportional to pressure and may be captured on capacitor 16 when the switches 14 are closed to the bridge 12. To sample the output stored on the capacitor 16, switches 14 may be opened and switches 34 may be closed to connect the capacitor 16 to the measurement electronics 40.

Ideally, but not necessarily essential, the reference sensor 20 will take the same form as the functional sensor. For example, as shown in FIG. 2A, the reference sensor 20 is shown to be a wheatstone bridge 22, but may also comprise a voltage divider. A wheatstone bridge has the advantage of self-compensation for drift of individual resistors, and is a good fit for integrated circuit applications. The wheatstone bridge 22 may comprise high stability discrete resistors, or may be imbedded in an integrated circuit constructed of polysilicon, diffused, thin film or other resistors. Operation of the high stability wheatstone bridge 22 is similar to the silicon piezoresistive wheatstone bridge 12 as mentioned above. The high stability wheatstone bridge 22 may be connected to the capacitor 16 via switches 24. The wheatstone bridge 22 may be fully contained within the reference sensor 20 as shown in FIG. 2A or completed elsewhere in the system such as electronics module 40.

It may be advantageous to connect early in the signal path to allow drift compensation for as much of the circuitry as possible. If the measurement electronics 40 are provided as an integrated circuit (chip or IC), and the reference sensor 20 is external to IC, the reference sensor 20 may be switched into the IC either externally or internally to the chip. If the IC already has a second pressure channel that is combined with a first pressure channel early in the signal path, the second channel may be permanently connected to the reference sensor 20 to provide a reference channel. Alternatively, the reference channel may be created on the IC by switching in an on-chip wheatstone bridge or by supplying an equivalent voltage to a switched capacitor amplifier (SC amp) using capacitors and charge redistribution. As a further alternative, the reference sensor 20 may comprise a low drift reference voltage such as a band-gap voltage source. In some circumstances, the reference sensor 20 could be created by shorting the outputs on the functional pressure sensor 10, but this may not be optimum for sensors that have high intrinsic offset that would not be represented by a shorted output.

Figure 2B:
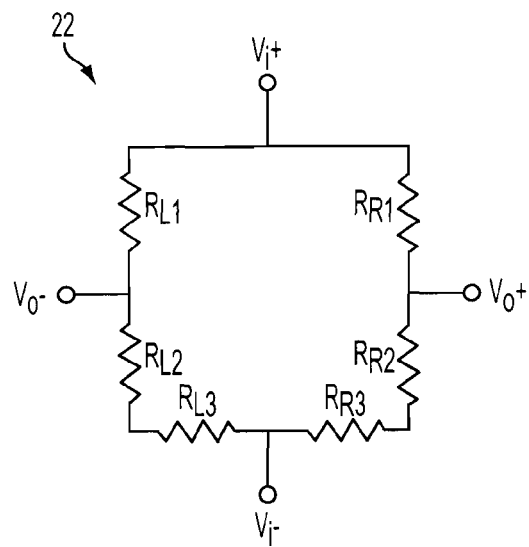
Figure 2C:
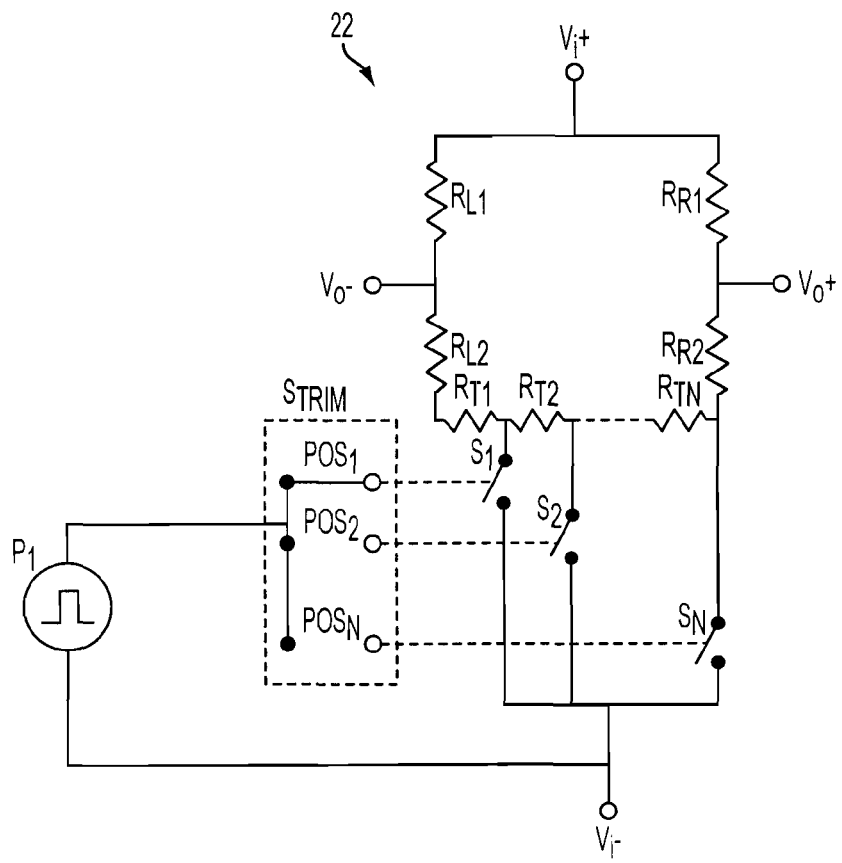

A functional sensor may have a high level of voltage offset between $V_o+$ and $V_o-$ that may vary significantly between sensors. For the reference sensor 20 to effectively compensate for drift of all components of the measurement system, it may match the characteristics of the functional sensor including resistance, capacitance, and voltage offset. With reference to FIGS. 2B and 2C, the reference sensor may have a capability to be trimmed such that it best matches a type of functional sensor or an individual functional sensor. FIG. 2C represents one method for trimming the voltage offset of the reference sensor to match that of a functional sensor. FIG. 2C also includes the capability to pulse the voltage supply to the sensor from the pulsatile voltage source P1. The pulsatile voltage source is routed to one of a set of switches $S_1$ through $S_N$. The switch selection changes the offset voltage ($V_o+$-$V_o-$) by adding differing amounts of resistance to $R_{L2}$ and $R_{R2}$.

In the case where the measurement electronics may be susceptible to drift of gain, two or more measurements of the reference sensor could be taken at two or more trim settings to calculate a reference value for the gain of the measurement circuit. This gain reference value can be compared over time to correct for gain drift similar to the methods described for use of the offset reference value to correct for offset drift.

The reference channel may be sampled in several different ways. Assuming the channels are sampled in time slots, a portion of the time slots allocated for the measurement channel may be sacrificed for the reference channel (substitution approach), or additional time slots may be provided for the reference channel without sacrificing time slots for the measurement channel (addition approach). With both the substitution and addition approaches, the reference channel time slots may be interleaved (e.g., every other, every third, every $n^{th}$) with the measurement channel time slots, or may occur at predetermined intervals to preserve battery capacity. If the transmitter in the telemetry unit 50 is activated only intermittently to send a burst of data, the reference channel may be sampled only during a predetermined time within or preceding the burst, either alternately with the measurement channel (addition approach) or instead of the measurement channel (substitution approach).

The measurement from the reference channel may be utilized in several different ways to reduce long-term drift. It may be compared to a reference channel calibration taken at manufacture to create an offset that is applied to functional channel measurements. Alternatively, the functional channel calibrations at manufacture may be taken relative to the reference channel. Then, in subsequent measurements, the reference channel may be measured and utilized in the application of the calibrations to the functional channel measurements which will automatically compensate for drift.

Figure 3:
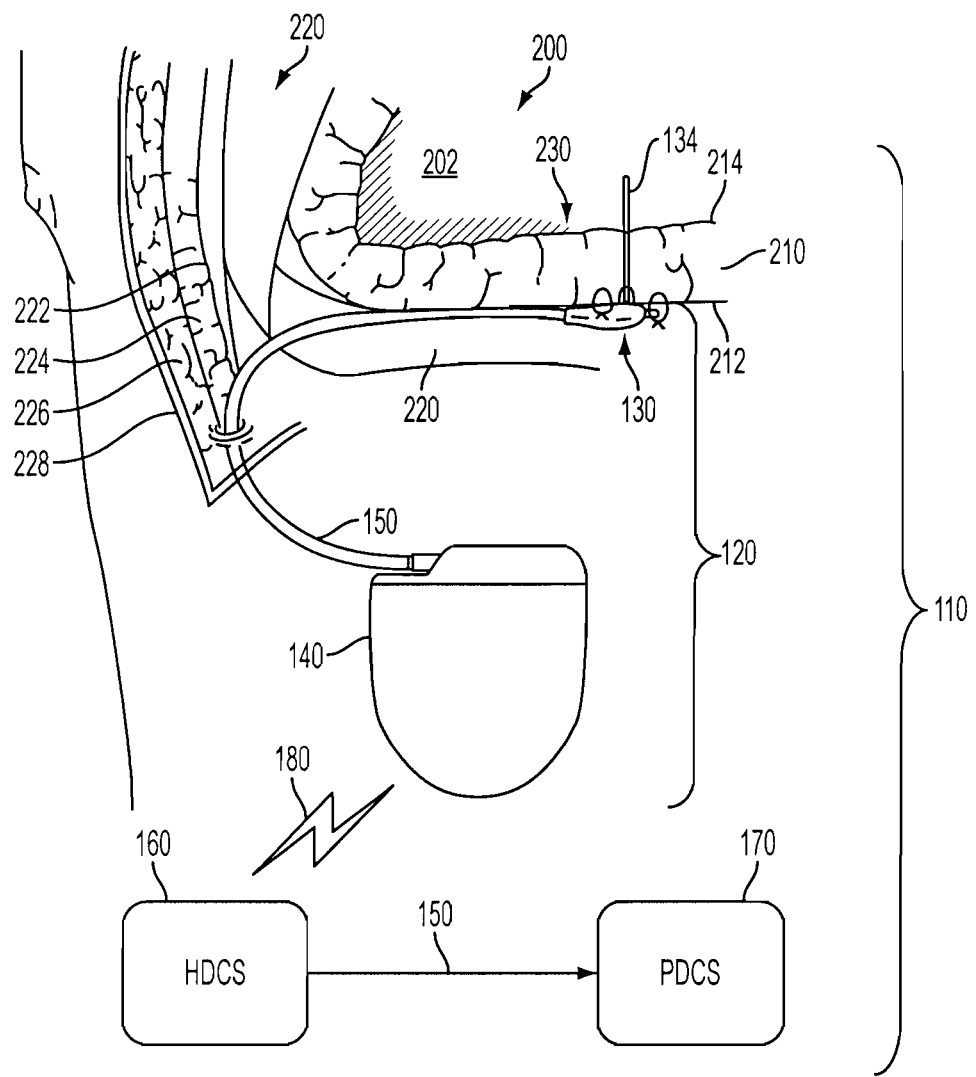
FIG. 3 schematically illustrates an example of an IMD system having a remote sensor assembly (RSA) that incorporates a functional pressure sensor and a reference sensor.
Figure 4:
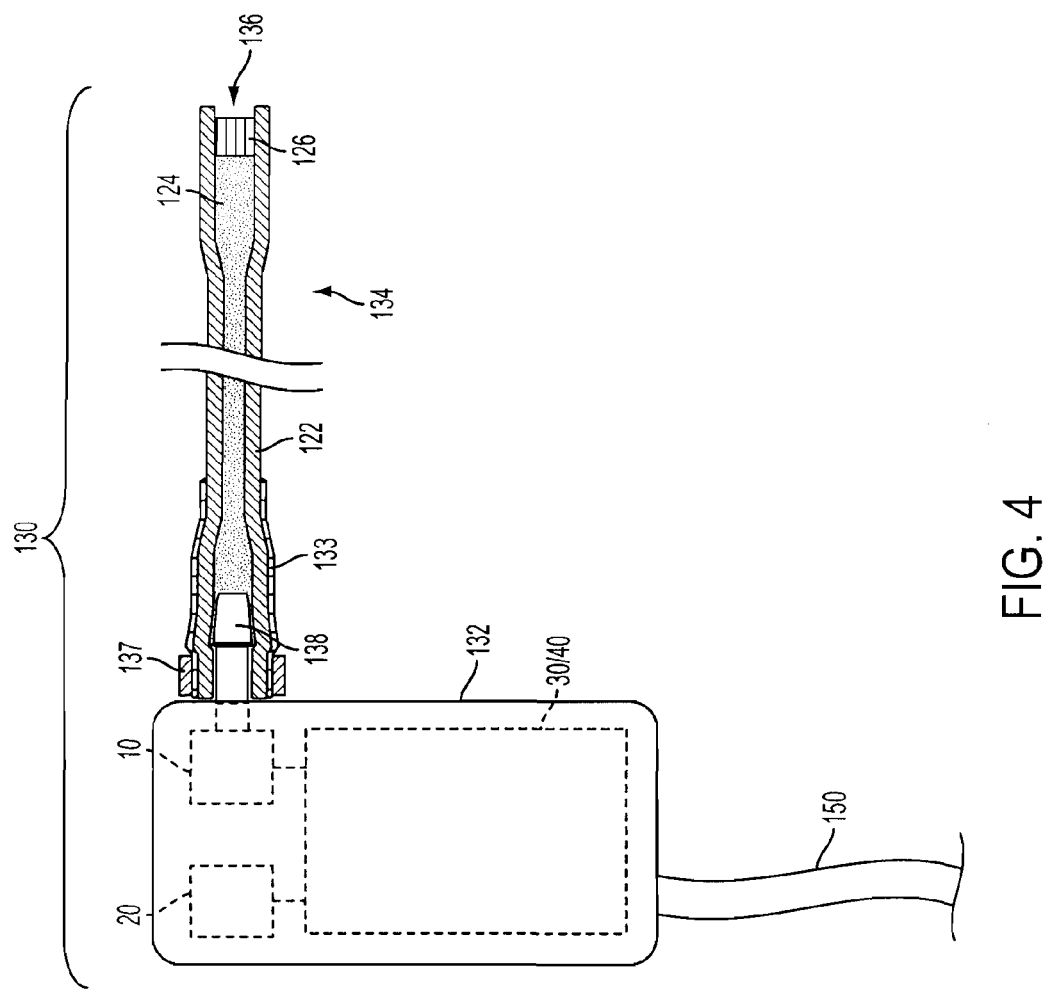
FIG. 4 is a schematic view of the RSA shown in FIG. 3, including a pressure transmission catheter shown in longitudinal cross-section.
Figure 5:
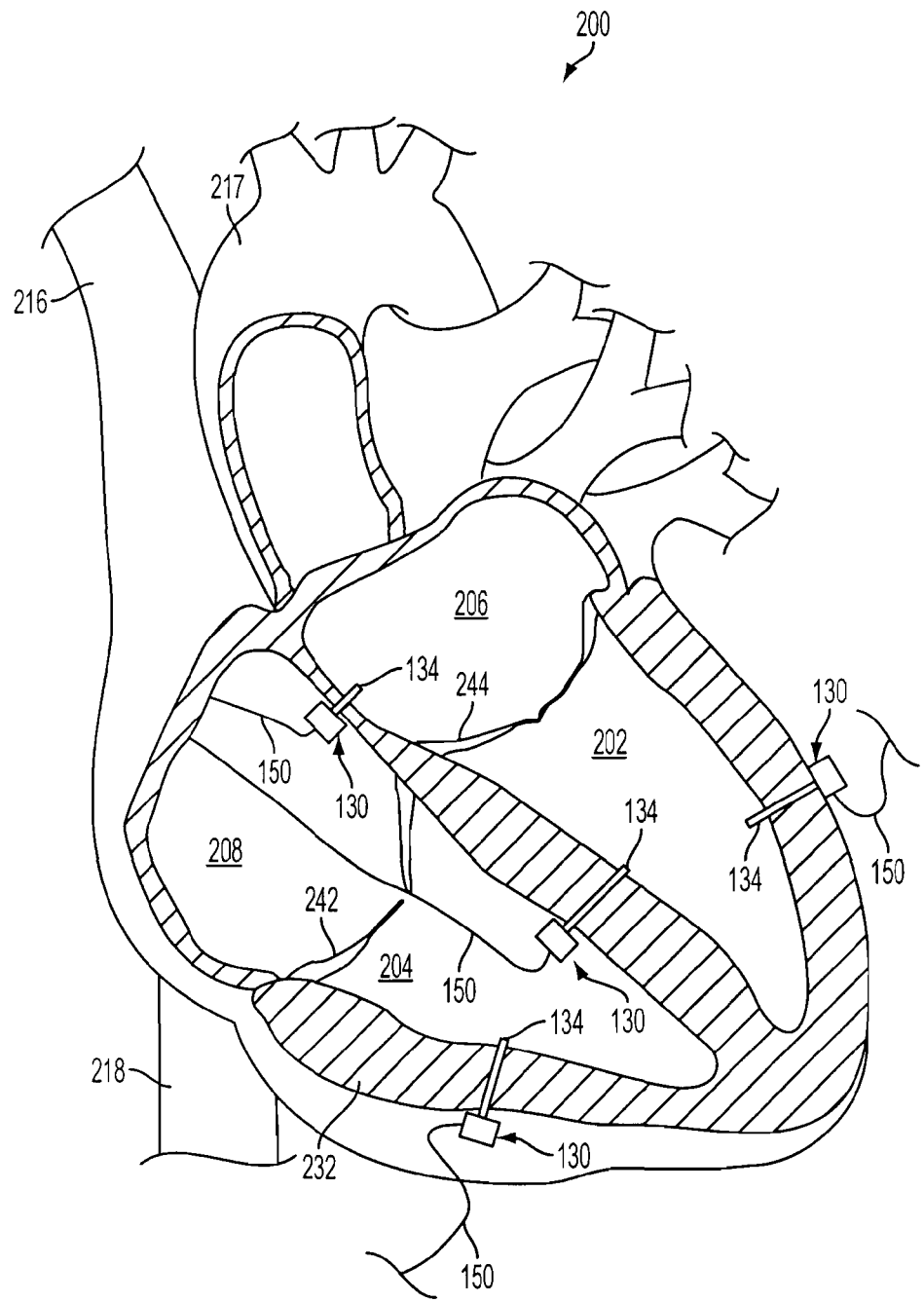
FIG. 5 schematically illustrates various possible endocardial implant locations for the RSA of the system shown in FIG. 3.

FIGS. 3-5 illustrate an example of an IMD system 110 that incorporates a reference sensor 20 and a functional sensor 10 to measure endocardial pressure. The illustrated system 110 is given by way of example, not necessarily limitation, to demonstrate how the reference sensor 20 and the functional sensor 10 may be incorporated into an IMD system. Those skilled in the art will recognize that the reference sensor 20 and the functional sensor 10 may be incorporated into other IMD systems not specifically mentioned herein.

With reference to FIG. 3, an exemplary embodiment of a system 110 for measuring and monitoring endocardial pressure is shown. The system 110 includes an implantable telemetry device (ITD) 120, which may be partitioned into a remote sensor assembly (RSA) 130 and a telemetry unit (TU) 140 interconnected via lead 150. An alternative construction (not shown) of the ITD 120 mounts the RSA 130 and TU 140 components in a single unit which may be implanted in a manner similar to RSA 130. The RSA 130 measures endocardial pressure and the TU 140 transmits measured pressure data to a receiver located outside the body via wireless telemetry link 180.

The system 110 also includes a home (i.e., local) data collection system (HDCS) 160 which receives the telemetry signal from the TU 140 via wireless link 180. The TU 140 may correct for fluctuations in ambient barometric pressure, may evaluate the validity of the received signal, and, if the received signal is deemed to be valid, may extract parameters from that signal and store the data according to a physician-defined protocol.

The system 110 further includes a physician (i.e., remote) data collection system (PDCS) 170 which receives the data signal from the HDCS 160 via a telecommunication link 190 (e.g., the Internet). The PDCS 170 may evaluate the validity of the received signal and, if the received signal is deemed to be valid, may display the data, and store the data according to a physician-defined protocol. With this information, the system 110 enables the treating physician to monitor endocardial pressure in order to select and/or modify therapies for the patient to better treat diseases such as CHF and its underlying causes.

For example, the system 110 may be used for assessment of pressure changes (e.g., systolic, diastolic, min dP/dt, and max dP/dt) in the main cardiac pumping chamber, the left ventricle (LV). These pressures are known to fluctuate with clinical status in CHF patients, and they provide key indicators for adjusting treatment regimens. For example, increases in end-diastolic pressure, changes in the characteristics of pressure within the diastolic portion of the pressure waveform, and decreases in max dP/dt, or increases in minimum dP/dt together suggest a deteriorating cardiac status. With this information, the physician is able to promptly and remotely adjust treatment. In addition, the system 110 may assist the physician in management of patients when newer forms of device therapy (e.g., multiple-site pacing, ventricular assist as a bridge to recovery, or implantable drugs pumps) are being considered.

With additional reference to FIG. 4, the RSA 130 includes a functional sensor 10 comprising a pressure transducer, a reference sensor 20, a switching circuit 30, and an electronics module 40 contained within a housing 132. The RSA 130 further includes a pressure transmission catheter (PTC) 134 extending from the housing 132. The RSA housing 132 protects the pressure transducer and the electronics module from the harsh environment of the human body. The RSA housing 132 may be fabricated of a suitable biocompatible material such as titanium or ceramic and may be hermetically sealed.

The pressure transducer 10 may be of the piezoresistive, or resonant structure. For example, the pressure transducer may comprise a piezoresistive wheatstone bridge type silicon strain gauge available from Sensonor of Horton, Norway. Examples of suitable pressure transducers are disclosed in U.S. patent application Ser. No. 10/717,179, filed Nov. 17, 2003, entitled Implantable Pressure Sensors, the entire disclosure of which is incorporated herein by reference. The electronics module may provide excitation to the pressure transducer 10, amplify the pressure signal, and digitally code the pressure information for communication to the TU 140 via the flexible lead 150. The electronics module may also provide for temperature compensation of the pressure transducer 10 and provide a calibrated pressure signal. A temperature measurement device may be included within the electronics module to compensate the pressure signal from temperature variations.

The proximal end of the RSA housing includes an electrical feedthrough to facilitate connection of the electronics module to the flexible lead 150. The distal bottom side of the housing includes a pressure transducer header to facilitate mounting of the pressure transducer and to facilitate connection to a pressure transmission catheter (PTC) 134.

The flexible lead 150 connects the electronics module of the RSA 130 to the telemetry electronics disposed in the TU 140. The lead 150 may contain, for example, four conductors—one each for power, ground, control in, and data out. The lead 150 may incorporate conventional lead design aspects as used in the field of pacing and implantable defibrillator leads.

The TU 140 includes telemetry electronics (not visible) contained within housing. The telemetry electronics disposed in the TU 140 may be the same or similar to those described in U.S. Pat. Nos. 4,846,191, 6,033,366, 6,296,615 or PCT Publication WO 00/16686, all to Brockway et al. The TU housing protects the telemetry electronics from the harsh environment of the human body. The TU housing may be fabricated of a suitable biocompatible material such as titanium, ceramic, or a combination thereof, and is hermetically sealed. Examples of other suitable housing designs are disclosed in U.S. Provisional Patent Application No. 60/438,712, filed Jan. 7, 2003, entitled Housing For Implantable Telemetry Device, the entire disclosure of which is incorporated herein by reference. The outer surface of conductive (i.e., metallic) portions of the TU housing may serve as an EGM sensing electrode. If a non-conductive material such as ceramic is used for the housing, conductive metal pads may be attached to the surface thereof to serve as EGM sensing electrodes. The TU housing includes an electrical feedthrough to facilitate connection of the telemetry electronics to the lead 150.

The proximal end of the PTC 134 is connected to the pressure transducer 10 via a nipple tube 138 to establish a fluid path from the pressure transducer 10 to the distal end of the PTC 134. The PTC 134 thus refers pressure from the pressure measurement site to the pressure transducer 10 located inside the RSA housing. The PTC 134 may comprise a tubular structure with a liquid-filled lumen extending therethrough to a distal opening or port.

A barrier 126 such as a gel plug and/or membrane may be disposed in or over the distal opening 136 to isolate the liquid-filled lumen 124 of the PTC 134 from bodily fluids and to retain the fluid in the lumen, without impeding pressure transmission therethrough. In one embodiment, the fluid 124 is chosen to be a fluorinated silicone oil and the gel is chosen to be dimethyl silicone gel. Further aspects of suitable fluids and gels are described in U.S. patent application Ser. No. 10/272,489, filed Oct. 15, 2002, entitled Improved Barriers and Methods for Pressure Measurement Catheters, the entire disclosure of which is incorporated herein by reference.

Further details and other aspects of the system 110 are described in U.S. patent application Ser. No. 10/077,566, filed Feb. 15, 2002, entitled Devices, Systems and Methods for Endocardial Pressure Measurement. Reference may also be made to U.S. Pat. No. 4,846,191 to Brockway et al., U.S. Pat. No. 6,033,366 to Brockway et al., U.S. Pat. No. 6,296,615 to Brockway et al., and PCT Publication WO 00/16686 to Brockway et al. for examples of alternative embodiments.

As seen in FIG. 3, the ITD 120 may be surgically implanted in/on a heart 200 of a patient. In this exemplary embodiment, the PTC 134 is inserted directly into the left ventricle (LV) 202 across the left ventricular wall 230 for the purpose of measuring LV pressure. In particular, the RSA housing resides on the epicardial surface 212 in the pericardial space defined by pericardium 220, with the PTC extending across the epicardium 212, myocardium 210 and endocardium 214, and into the LV chamber 202. This allows for chronic monitoring of pressure in the LV chamber 202 of the heart 200.

Implantation of the ITD 120, including RSA 130 and TU 140, may take place during an open chest procedure such as would normally be done to perform coronary artery bypass or valve repair/replacement. Alternatively, the ITD 120 may be implanted in a separate surgical procedure. In such a case, the surgeon performs a median sternotomy, cutting across the dermal layer 228, sub-dermal tissue layer 226, muscle layer 224, and sternum 222. The surgeon then cuts the pericardial sac 220 to expose the heart 200, down to the LV apex.

The PTC 134 is introduced into the LV 202 at the inferior apical segment using a peelable-sheath introducer and a trocar. The peelable-sheath introducer facilitates insertion of the PTC 134 into the myocardium 210 and protects the PTC 134 from damage that may otherwise occur during the insertion process. Following insertion of the PTC 134, the peelable-sheath introducer is removed by peeling it off the PTC 134 and around the RSA housing. A sheath retainer may be used to prevent splitting of the introducer inside the heart wall and to hold the RSA 130 in place while the introducer is removed. The PTC 134 is automatically positioned within the LV 202, in terms of depth, by virtue of its length when the housing of the RSA 130 contacts the epicardial surface.

The proximal lead 150 is then draped over the open pericardial edge, and brought caudally inferior laterally under the abdominal fascia. A 4-5 cm horizontal incision is made on the left upper quadrant of the abdominal wall and a subcutaneous pocket is created. The proximal end of the flexible lead 150 may be brought into the subcutaneous pocket through an introducer placed through the abdominal fascia. If a releasable connection is utilized, the lead 150 is attached to the TU 140, tested using a PDCS 170, and the TU 140 is placed in the subcutaneous pocket. The pocket and the chest are then closed.

With specific reference to FIG. 4, further details of the RSA 130 are shown schematically and described below. The RSA housing 132 contains the electronics module 40 which, in this example, incorporates switching circuit 30. The RSA housing 132 also contains the functional sensor or pressure transducer 10 and the reference sensor 20, both of which are connected to the switch and electronics module 30/40.

The PTC 134, which is shown in longitudinal cross-section, may comprise a tubular shaft 122 with a liquid-filled lumen 124 extending therethrough to a distal opening or port 136 containing a barrier plug 126. The proximal end of the PTC 134 is connected to the pressure transducer 10 in the RSA 130 via nipple tube 138. The PTC 134 refers pressure from the distal port 136 via plug 126 and liquid-filled lumen 124 to the pressure transducer 10 of the RSA 130 via a lumen extending through nipple tube 138.

The proximal end of the PTC 134 may include an interlocking feature to secure the PTC 134 to the nipple tube 138. For example, the nipple tube may have an enlarged head as shown, or may have a knurled surface, raised rings or grooves, etc. A compression band 137 may be disposed around the proximal end of the PTC 134 to provide compression onto the interlocking feature of the nipple tube 138. The compression band 137 may comprise a polymeric or metallic (e.g., shape memory NiTi) band, a spring coil, etc., to provide compression onto the nipple tube 138.

The PTC 134 may comprise a wide variety of materials, constructions and dimensions depending on the particular clinical application and the bodily tissue in which the PTC 134 resides when implanted. For example, the PTC 134 may comprise an extruded polyurethane (e.g., Bionate™) tube with a thermally formed proximal flare to accommodate the nipple tube 138, and a thermally formed distal flare to reduce pressure measurement errors due to motion artifacts and thermal expansion artifacts. The PTC 134 may also incorporate a polyester fabric tube 133 or other surface modification. The PTC 134 may be annealed to improve its mechanical properties and may be etched in solvent to remove frayed edges.

By way of example, not limitation, the PTC 134 may have an overall length of approximately 26 mm, a proximal flare length of approximately 6.0 mm, a distal flare length of approximately 5.5 mm, tapered transition lengths of approximately 2.0 mm, a mid-shaft inside diameter of approximately 0.025 inches, a proximal flare inside diameter of approximately 0.038 inches increasing to 0.059 inches to accommodate the nipple tube 38, a distal flare inside diameter of approximately 0.042 inches, and a wall thickness of approximately 0.015 inches, which are particularly suitable for LV pressure monitoring applications as shown and described with reference to FIG. 3. Various different lengths, diameters, tapers, flares, wall thicknesses, coatings, coverings, surface treatments, etc. may be incorporated into the PTC 134 depending on the application without departure from the present invention. Further details and alternative embodiments of the PTC 134 are described in U.S. patent application Ser. No. 10/799,931 filed Mar. 12, 2004 entitled Pressure Transmission Catheter for Implantable Pressure Sensors, which is incorporated herein by reference.

With reference to FIG. 5, various possible anatomical implant positions for the RSA 130 are shown. To facilitate a discussion of the various possible anatomical implant positions, the heart 200 is shown schematically. The heart 200 includes four chambers, including the left ventricle (LV) 202, the right ventricle (RV) 204, the left atrium (LA) 206, and the right atrium (RA) 208. The LV 202 is defined in part by LV wall 230, and the RV 204 is defined in part by RV wall 234. The LV 202 and the RV 204 are separated by ventricular septal wall 232, and the LA 206 and the RA 208 are separated by atrial septal wall 236.

The right atrium 208 receives oxygen deprived blood returning from the venous vasculature through the superior vena cava 216 and inferior vena cava 218. The right atrium 208 pumps blood into the right ventricle 204 through tricuspid valve 242. The right ventricle 204 pumps blood through the pulmonary valve and into the pulmonary artery which carries the blood to the lungs. After receiving oxygen in the lungs, the blood is returned to the left atrium 206 through the pulmonary veins. The left atrium 206 pumps oxygenated blood through the mitral valve 244 and into the left ventricle 202. The oxygenated blood in the left ventricle 202 is then pumped through the aortic valve, into the aorta 217, and throughout the body via the arterial vasculature.

By way of example, not limitation, the RSA 130 may be implanted such that the distal end of the PTC 134 resides in any chamber of the heart 200, such as the LV 202 or the LA 206, for example, although the LV 202 is preferred for some clinical applications. For example, the PTC 134 may be positioned across the LV wall 230 such that the distal end of the PTC 134 is disposed in the LV 202 as described with reference to FIG. 3. As an alternative, the PTC 134 may be positioned across the RV wall 234 such that the distal end of the PTC 134 is disposed in the RV 204. As a further alternative, the PTC 134 may be positioned across the atrial septal wall 236 or the ventricular septal wall 232 such that the distal end of the PTC 134 is disposed in the LA 206 or LV 202, respectively. If the ITD 120 comprises a unitary structure containing both the RSA 130 and the TU 140, the ITD 120 may be positioned in the same manner as the RSA 130 or it may be entirely disposed within a heart chamber.

Although endocardial implant sites are shown and described herein, the RSA 130 may be implanted such that the PTC 134 extends through a vascular wall and into a vascular lumen, with the RSA housing and associated components disposed outside the vascular wall. Further aspects of this vascular approach are described in U.S. Provisional Patent Application No. 60/440,151, filed Jan. 15, 2003, entitled Therapeutic Device and Method Using Feedback from Implantable Sensor Device, the entire disclosure of which is incorporated herein by reference.

From the foregoing, it will be apparent to those skilled in the art that the present invention provides, in exemplary no-limiting embodiments, IMD systems and methods for measuring a body parameter utilizing an implantable functional sensor and a fixed reference sensor, wherein the reference sensor compensates for drift of all electronic components in the measurement system other than the functional sensor. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A pressure sensing system for measuring a variable body parameter, comprising:

an implantable functional pressure sensor configured to measure a variable body parameter;

a reference circuit of the same form as the functional sensor, that when measured provides an output that is relatively constant;

an electronic measurement circuit connected to the functional sensor and to the reference circuit, and operable to measure an output provided by either the functional sensor or the reference circuit, wherein at least a portion of the electronic measurement circuit is subject to measurement drift over time; and a corrector which corrects for said measurement drift as a function of a measurement by the measurement circuit of the reference circuit.

2. A pressure sensing system as in claim 1, wherein the reference circuit is subject to less drift over time than the electronic measurement circuit.

3. A pressure sensing system as in claim 1, wherein:
the functional sensor converts the variable body parameter into an electronically measurable parameter with a value that varies as a function of the body parameter, and
the reference circuit has the same electronically measurable parameter with a value that is constant.

4. A pressure sensing system as in claim 1 wherein:
the functional sensor converts the variable body parameter into an electronically measurable parameter with a value that varies as a function of the body parameter, and
the electronically measurable parameter comprises resistance.

5. A pressure sensing system as in claim 4, wherein:
the functional sensor is piezoresistive; and
the reference circuit comprises one or more resistors.

6. A pressure sensing system as in claim 1, wherein:
the functional sensor converts the variable body parameter into an electronically measurable parameter with a value that varies as a function of the body parameter; and
the electronically measurable parameter comprises voltage.

7. A pressure sensing system as in claim 1, wherein:
the functional sensor converts the variable body parameter into an electronically measurable parameter with a value that varies as a function of the body parameter, and
the electronically measurable parameter comprises current.

8. A pressure sensing system as in claim 1, wherein the pressure sensor comprises a piezoresistive type sensor.

9. A pressure sensing system as in claim 8, wherein the reference circuit comprises one or more resistors.

10. A pressure sensing system as in claim 9, wherein the resistors comprise highly stable resistors.

11. A pressure sensing system as in claim 9, wherein the reference circuit comprises a wheatstone bridge.

12. A pressure sensing system as in claim 9, wherein the reference circuit is contained in an integrated circuit.

13. A pressure sensing system as in claim 1, wherein the electronic measurement circuit includes a switched measurement channel for selective connection to the functional sensor and reference circuit.

14. A pressure sensing system as in claim 1, wherein the electronic measurement circuit includes first and second measurement channels, with the first channel connected to the functional sensor and the second channel connected to the reference circuit.

15. A pressure sensing system as in claim 1, wherein the corrector subtracts a current value of the reference circuit from a prior value of the reference circuit.

16. A pressure sensing system as in claim 15, wherein the current value is different than the prior value and the difference represents measurement drift of the electronic measurement circuit, and wherein a measurement of the functional sensor is corrected as a function of the difference.

17. The pressure sensing system as in claim 1, wherein the body parameter correlates to values measured by the functional sensor according to a predetermined transfer function.

18. A pressure sensing system as in claim 17, wherein the transfer function is corrected as a function of a current value of the reference circuit.

19. A pressure sensing system as in claim 1, wherein the corrector comprises hardware.

20. A pressure sensing system as in claim 1, wherein the corrector comprises software.

21. A pressure sensing system as in claim 1, wherein the electronic measurement circuit includes the corrector.

22. A pressure sensing system as in claim 1, wherein a data collection and processing unit includes the corrector.

23. A pressure sensing system as in claim 1, wherein the reference circuit has electrical characteristics that match electrical characteristics of the functional sensor.

24. A pressure sensing system as in claim 1, wherein the reference circuit includes electrical components that match electrical components of the functional sensor, and wherein the electrical components of the reference sensor are interconnected to form an arrangement that matches an arrangement of electrical components of the primary sensor.

25. A pressure sensing system as in claim 24, wherein the arrangement is a wheatstone bridge.

26. A method of measuring a variable body parameter with an implantable pressure sensor including a functional sensor and an electronic measurement circuit, the method comprising:
obtaining a functional measurement of the variable body parameter utilizing the functional sensor and the electronic measurement circuit;
obtaining a reference measurement utilizing a reference circuit and the electronic measurement circuit, wherein the reference circuit has a relatively constant value; and
correcting the functional measurement for drift of the electronic measurement circuit based on the reference measurement.

27. A method as in claim 26, wherein the reference circuit has a drift rate less than the drift rate of the electronic measurement circuit.

28. A method as in claim 26, wherein the functional measurement is made by sampling the functional sensor at a desired time, and wherein the reference measurement is made by sampling the reference circuit at two or more times.

29. A method as in claim 26, wherein the reference measurement is made by switching the electronic measurement circuit from the functional sensor to the reference circuit.

30. A method as in claim 26, further comprising:
comparing a current reference measurement to a prior reference measurement to obtain a difference representing drift of the electronic measurement circuit; and
applying the difference to the functional measurement.

31. A method as in claim 26, further comprising applying a transfer function to correlate the functional measurement to a value representative of the body parameter.

32. A method as in claim 31, further comprising:
obtaining a current reference measurement representing drift of the electronic measurement circuit; and
applying the current reference measurement to the transfer function.

* * * * *